United States Patent [19]

Bannard et al.

[11] Patent Number: 5,075,297

[45] Date of Patent: Dec. 24, 1991

[54] BROAD SPECTRUM CHEMICAL DECONTAMINANT SYSTEM

[75] Inventors: Robert A. B. Bannard, Carp; Alfred A. Casselman, Greely; John G. Purdon; John W. Bovenkamp, both of Kanata, all of Canada

[73] Assignee: Her Majesty the Queen in right of Canada, as represented by the Minister of National Defence in Her Majesty's Canadian Government, Ottawa, Canada

[21] Appl. No.: 700,922

[22] Filed: Nov. 20, 1984

[30] Foreign Application Priority Data

Nov. 22, 1983 [CA] Canada .................................. 441616

[51] Int. Cl.$^5$ ............................ A62D 5/00; A61K 7/40
[52] U.S. Cl. ...................................... 514/183; 514/640; 514/723; 514/731; 514/969
[58] Field of Search ............... 514/640, 723, 731, 969, 514/183

[56] References Cited

U.S. PATENT DOCUMENTS

| | | | |
|---|---|---|---|
| 2,391,798 | 12/1945 | Read | 514/731 |
| 3,011,940 | 12/1961 | Bollenback | 514/731 |
| 3,179,563 | 4/1965 | Roberts | 514/640 X |
| 3,800,051 | 3/1974 | Barnhart et al. | 514/731 |
| 4,239,781 | 12/1980 | Edwards | 514/723 |

OTHER PUBLICATIONS

*The Condensed Chemical Dictionary*, Sixth Edition, Pub. 1961, Reinhold Pub. Co., New York, p. 1049.

*Primary Examiner*—Robert L. Stoll
*Assistant Examiner*—Gary L. Geist
*Attorney, Agent, or Firm*—Nixon & Vanderhye

[57] ABSTRACT

A protective system against chemical warfare agents consisting essentially of at least one alkali metal salt of phenol, acetone oxime, acetophenone oxime and 2,3-butanedione monoxime, a macrocycle chosen from 18-crown-6 or cryptand [2,2,2] and a solvent chosen from dioxolane, tetraglyme, dimethoxyethane, a polyethylene glycol or a polyethylene glycol mono- or diether the system also containing just enough water to dissolve the active ingredient. These systems afford protection against mustard gas (H or HD) and against chemical warfare agents of the V and G types.

14 Claims, No Drawings

BROAD SPECTRUM CHEMICAL DECONTAMINANT SYSTEM

This invention relates to a barrier cream formulation which can be used to protect exposed areas of the body from the effects of chemical warfare agents.

Three types of chemical warfare agents which are considered to constitute a major threat are those commonly designated as H or HD, V and G. The first of these, H or HD is mustard gas, the 'D' implying that it has been distilled. This substance is 2,2'-dichlorodiethylsulphide, $(ClCH_2CH_2)_2S$. It belongs to the vesicant class of chemical warfare agents. The V and G series are both nerve agents. The G series tend to be volatile and highly toxic by inhalation, whilst the V-agents are generally non-volatile, persistent and highly toxic by the percutaneous route. Typical examples of these series are GD and VX of the following formulae.

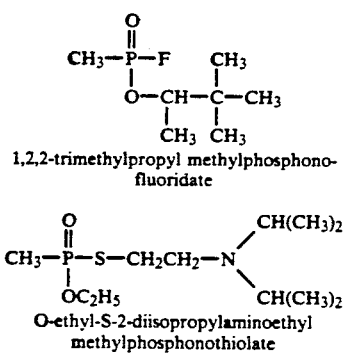

1,2,2-trimethylpropyl methylphosphonofluoridate

O-ethyl-S-2-diisopropylaminoethyl methylphosphonothiolate

To be of any use in practical field conditions, any barrier cream which is to be used as a protection against chemical warfare agents has to exhibit three main properties. First, it must be effective against all three of these types of chemical warfare agents. Second, it must be compatible with human skin and not cause any adverse reactions, at least over a limited period of time. Third, it must provide protection to the wearer for a reasonable period of time. These three criteria effectively exclude many of the currently known decontamination systems which have been devised from time to time as a means of destroying chemical warfare agents. The chief difficulty is that such decontamination systems contain reagents which cannot be tolerated on human skin for any more than quite brief periods of time. Some of these systems are very alkaline, and some use concentrated active chlorine, bleach solutions. Thus, although these systems are, more or less, effective as decontaminants for equipment which has been exposed to chemical warfare agents, they are of little use in protecting people, and give no guide at all to the sort of reagents that may be used for this purpose.

It has long been realised that these chemical warfare agents were susceptible to nucleophilic attack. Several earlier proposals for both decontaminant formulations and protective cream-type formulations have adopted this approach. But generally these proposals have failed to overcome two somewhat unrelated problems. One problem is techniques whereby the nucleophilic reagent can be obtained in a relatively pure state, and free of any skin-damaging contaminants. For example, whilst potassium phenoxide appears to be a potentially useful reagent for this purpose, it has not hitherto generally been found possible to prepare this salt by a simple technique which will provide a product free of potassium hydroxide. The second commonly encountered difficulty is that for such a protective system both to be effective against a reasonable level of attack, in terms of the amount of chemical warfare agent to which a given area of skin is exposed, and to provide protection for a reasonable period of time, a more than minimal solubility of the reagent in the protection system is required. To be of practical field use, it has to be possible to utilise a reasonably thin layer of the protection system. The systems that have hitherto been proposed cannot do this.

We have now found a surprisingly simple and efficacious solution to this problem which permits the formulation of a barrier cream which is effective against all three types of agents, causes no adverse skin reactions to occur over the periods of time that such a barrier cream is likely to be worn, and also provides the wearer with protection for a reasonable period of time. A particular feature of the creams of this invention is that although they contain potentially powerful nucleophilic agents, such as, for example, potassium phenoxide, they do appear to be compatible with human skin.

Thus, in its broadest aspect, this invention provides a protective system consisting essentially of at least one active ingredient chosen from the alkali metal salts of phenol, acetone oxime, acetophenone oxime, and 2,3-butanedione monoxime, the active ingredient being dispersed in a base comprising a macrocycle chosen from 1,4,7,10,13,16-hexaoxacyclooctadecane and 4,7,13,16,21,24-hexaoxa-1,10-diazabicyclo[8.8.8]hexacosane together with a solvent chosen from dioxolane, tetraglyme, dimethoxyethane, a polyethylene glycol, or a polyethylene glycol mono- or di-ether the base further including just sufficient water to ensure dissolution of the active ingredient in the base.

Preferably the alkali metal salts are those of sodium and potassium, the potassium salts being the most preferred.

Preferably the active ingredient is a phenol salt, the most preferred phenol salt being potassium phenoxide.

Preferably the base contains substantially equal amounts of the macrocycle and of the active ingredient. Generally the amount of water included is small, and will not exceed 5% of the base. It is desirable that the amount of water present be kept to a minimum as otherwise unwanted side reactions between the active ingredient and the water may occur. Ideally, the base will contain no water at all.

Reference was made above to a polyethlene glycol or polyethylene glycol ether. These compounds have the formula $R-O-(CH_2CH_2O)_nCH_2CH_2OR$ in which either R may be hydrogen or an alkyl group, usually methyl or ethyl, and n indicates the chain length. For this invention n can have a range of values. As n increases, the compound becomes more viscous. At a value to give a molecular weight of 1500 no further thickening agent would likely be needed. Preferably at least one of the R groups, and most preferably both, are other than hydrogen, and are typically methyl or ethyl. Reference was also made above to the compound known as tetraglyme. The full chemical formula for this substance is $CH_3OCH_2CH_2O_3CH_2CH_2OCH_3$. It is thus the dimethyl ether of tetraethylene glycol. Reference is also made above to two macrocyclic systems. These both have simpler trivial names which will be used hereafter. The octadecane is known as 18-crown-6, and the bicyclohexacosane as cryptand [2,2,2].

In practice, it is found that most of the three component systems defined above are too fluid to use as a cream formulation. This problem is easily overcome by including in the formulation a pharmaceutically acceptable inert solid as a thickener, which is also inert toward the active ingredient of these creams. Typical usable solids are silicas, titania, fuller's earth, clays, bentonite and so forth. We prefer to use a pyrogenic silica, such as Cab-O-Sil (trade mark). It is to be noted, however, that an "active" silica containing hydroxyl groups may need to be etherified before use.

The barrier creams of this invention also proffer a further unexpected advantage. It as noted above that the equipment decontamination systems commonly used cannot be used on skin due to their chemical nature. This also means that such systems tend to be of questionable use for decontaminating porous equipment surfaces, such as fabrics and webbing. If these chemical solutions are left in contact with such porous materials long enough to penetrate them adequately, then they are also apt to damage the material as well. This is not the case with the creams of this invention, which can be left in contact with porous contaminated surfaces for extended periods of time without any damage resulting. For this application of the creams of this invention, a stable foam formulation of the type commonly used in shaving creams and the like is also advantageous.

It is noted above that the barrier creams of this invention do not affect the skin. It is believed that this is, at least in part, due to the fact that the salts used are free of base: for example, the potassium phenoxide used is free, substantially, of potassium hydroxide. We have devised a technique whereby these active ingredients can be made in a substantially pure state, containing only insignificant amounts, if any, of the free alkali metal hydroxide.

The invention will now be described by way of reference to the following Examples.

EXAMPLE 1

Preparation of Potassium Phenoxide

Phenol, 25 g, sublimed under vacuum, was dissolved in 150 ml dry ether and added by a dropping funnel to a stirred suspension of 9.21 g of powdered potassium in a dry mixture of toluene, 150 ml and ether, 150 ml. After 24 hours reflux, the mixture was filtered and a colourless solid obtained which was washed twice with dry ether. The salt was dried under high vacuum at 56° C. for 24 hours. M.p.: 285°–289° C. Analysis: K, theory: 29.57; found 29.08. Purification by dissolution in hot acetone, and precipitation with dry ether raised the K analysis figure to 29.17.

EXAMPLE 2

Preparation of Potassium Acetone Oximate

Acetone oxime, 30 g, dissolved in 250 ml dry ether was added dropwise to a suspension of 14.25 g powdered potassium in a mixture of 150 ml dry toluene and 150 ml dry ether. The mixture was refluxed for 48 hours. During this time a total of 400 ml of dry ether was added to facilitate stirring. After filtration and high vacuum drying, a colourless product was obtained. This was purified by dispersing 5 g of the solid in a mixture of acetone, 100 ml, and ethanol, 15 ml, at 50° C., filtering hot and precipitating the product by adding 300 ml of acetone. After allowing to stand for 15 minutes, the colourless salt was recovered by filtration and high vacuum dried, at 78° C. Analysis: K: theory 35.16; found: 35.01.

EXAMPLE 3

Potassium Acetophenone Oximate

Acetophenone Oximate 46 g, dissolved in 400 ml dry ether was added dropwise to a stirred suspension of 12.54 g powdered potassium in 150 ml dry toluene and 150 ml dry ether. After refluxing for 48 hours, and filtering, the solid was washed several times with dry ether, and dried under high vacuum. The solid was purified by dispersing 10 gm in a mixture of 50 ml acetonitrile and 100 ml dimethyl sulphoxide. The mixture was heated to 70° C., filtered hot, and allowed to cool. The colourless solid was collected by filtration, and dried under high vacuum at 56° C. for 24 hours. M.p.: 267°–270° C. Analysis: K: theory 22.57, found: 22.33.

EXAMPLE 4

Potassium 2,3-Butanedione Monoximate 35 g of 2,3-Butanedione monoximate was dissolved in 250 ml dry ether and added dropwise to a stirred suspension of 11.7 g powdered potassium in 150 ml dry toluene and 150 ml dry ether. A small amount (200 mg) of 1,4,7, 10,13,16-hexaoxacyclooctadecane was added, and the mixture refluxed for one week. The resulting yellow salt was filtered off, washed several times with dry ether, and dried under high vacuum. The solid was purified by dissolving 5 gm. in 100 ml of warm ethanol, filtering hot, and precipitating by adding 300 ml dry ether. After standing 30 min., the solid was collected by filtration, and dried under high vacuum at 78° C. M.p.: 224°–226° C. Analysis: K: theory, 28.09, found: 28.42.

EXAMPLE 5

Penetration of Mustard gas through barrier creams

The apparatus consists of a series of separate cells of circular cross-section over which approximately 2¼ inch-diameter samples of 0.022 mm-thick polyethylene film are cemented to rubber annuli, with an internal diameter of 2 inches. The annuli are 1 mm or 0.5 mm in depth. The cavities of these annuli are filled to the top with the cream to be tested, using a liquid filling technique following liquefaction of the creams by heating to 40°–50° C. After the solution has cooled and the cream has set, the samples are carefully examined for discontinuities, i.e. broken seals at the edge of the annuli or bubbles and if none are found the samples are placed in the test apparatus, 5×1 uL drops of mustard gas are applied by hypodermic needle touchoff to the surface of the cream in the usual manner and the amount of agent which penetrates the cream in 24 h is determined. The determination is made by sweeping air from the cavity below the polyethylene film and absorbing the mustard gas in a trapping solvent. This solution is then analyzed by a standard gas chromatography method to determine the amount of mustard gas that has penetrated both the cream and the polyethylene film.

The cream used was 0.625M potassium phenoxide in polyethyleneglycol 750 monomethyl ether (i.e. the monomethyl ether of a polyethyleneglycol having an average molecular weight of 750) containing the macrocycle 18-crown-6, in equimolar proportion to the potassium phenoxide. The following results were obtained.

| Film Thickness, | Average Mustard Gas Penetration, ug | |
|---|---|---|
| mm | Control | Test Film |
| 1.0 | 457 (1) | 0 (1) |
| 1.0 | 386 (2) | (0) (2) |
| 0.5 | 386 (2) | 11.7 (3) |

(1) 3 samples
(2) 2 samples
(3) 4 samples

EXAMPLE 6

In this Example the efficacy of liquid systems which can be converted into cream by, for example, the addition of pyrogenic silica were tested to assess their ability to destroy HD, VX and GD in a relatively short time. The test was conducted as follows.

An aliquot of an 0.2 molar solution of the active ingredient in a solvent was placed in a reaction vessel, the solution being approximately 0.2 molar with respect to both the active ingredient and the macrocycle. To this was added an aliquot of the agent, to provide a molar ratio active ingredient:macrocycle:agent of 8:8:1. The vessel was then stirred at 19°–22° C. for the specified time, and then quenched with a large excess of glacial acetic acid. The amount of agent then remaining, if any, was then determined by gas chromatography. In these tests, the reaction time was 5 mins.

Four active ingredients were tested, identified as follows in the table:

| System No. | Solvent (% water) | Active Ingredient | Macrocycle* | % Agent Destruction | | |
|---|---|---|---|---|---|---|
| | | | | HD | VX | GD |
| 1 | Dioxolane | A | 18.C.6 | 100 | 100 | 100 |
| 2 | Dioxolane | A | Cryp | 100 | 100 | 100 |
| 3 | Tetraglyme (2.5) | A | 18.C.6 | 100 | 100 | 100 |
| 4 | Tetraglyme (2.0) | A | Cryp | 100 | 100 | 100 |
| 5 | Dimethoxyethane (2.5) | A | 18.C.6 | 100 | 100 | 100 |
| 6 | Dimethoxyethane | A | Cryp | 100 | 100 | 100 |
| 7 | Dioxolane | B | 18.C.6 | 100 | 100 | 100 |
| 8 | Dioxolane | B | Cryp | 100 | 100 | 88 |
| 9 | Tetraglyme (3.0) | B | 18.C.6 | 100 | 100 | 100 |
| 10 | Tetraglyme (4.0) | B | Cryp | 100 | 100 | 100 |
| 11 | Dimethoxyethane (1.5) | B | 18.C.6 | 100 | 100 | 100 |
| 12 | Dimethoxyethane (1.25) | B | Cryp | 100 | 100 | 100 |
| 13 | Dioxolane | C | 18.C.6 | 100 | 100 | 100 |
| 14 | Dioxolane | C | Cryp | 100 | 100 | 88 |
| 15 | Tetraglyme (1.0) | C | Cryp | 100 | 100 | 100 |
| 16 | Dimethoxyethane (1.0) | C | Cryp | 100 | 100 | 100 |
| 17 | Dioxolane | D | 18.C.6 | 100 | 100 | 100 |
| 18 | Dioxolane | D | Cryp | 100 | 100 | 100 |
| 19 | Tetraglyme | D | Cryp | 100 | 100 | 100 |
| 20 | Dimethoxyethane | D | Cryp | 100 | 100 | 100 |

*18-C-6: 18-Crown-6
Cryp: Cryptand [2,2,2]
A. Potassium acetone oximate
B. Potassium acetophenone oximate
C. Potassium 2,3-butanedionemonoximate
D. Potassium Phenoxide.

EXAMPLE 7

A similar series of tests was run as in Example 6, to investigate the ratio of active ingredient:macrocycle:agent that is desirable. Using potassium acetone oximate in dioxolane, the following results were obtained.

| Ratio | Macrocycle | % Agent Destruction | | |
|---|---|---|---|---|
| | | HD | VX | GD |
| 8:8:1 | 18.C.6 | 100 | 100 | 100 |
| 8:4:1 | 18.C.6 | 100 | 100 | 99 |
| 4:2:1 | 18.C.6 | 45 | 100 | 23 |
| 2:1:1 | 18.C.6 | 21 | 12 | 2 |
| 8:8:1 | Cryp | 100 | 100 | 100 |
| 8:4:1 | Cryp | 100 | 100 | 100 |
| 4:2:1 | Cryp | 91 | 100 | 55 |
| 2:1:1 | Cryp | 48 | 15 | 7 |

Similar results were also obtained with potassium 2,3-butanedione oximate and potassium phenoxde. These results indicate that the creams should contain equal parts of the active ingredient and the macrocycle for maximum effectiveness.

The embodiments of the invention in which an exclusive property or privilege is claimed are defined as follows:

1. A protective system against chemical warfare agents consisting essentially of:
   (a) at least one active ingredient selected from the alkali metal salts of phenol, acetophenone oxime, acetone oxime, and 2,3-butanedione monoxime; together with a base comprising
   (b) a macrocycle selected from 1,4,7,10,13,16-hexaoxacyclooctadecane or 4,7,13,16,21,24-hexaoxa-1,10-diazabicyclo[8,8,8] hexacosane; and
   (c) a solvent selected from dioxolane, dimethoxyethane, a polyethylene glycol or an alkyl substituted polyethylene glycol mono- or di-ether, together with up to 5% water to ensure dissolution of the active ingredient in the base.

2. A protective system according to claim 1 further containing an inert solid thickener to provide a creamy consistency.

3. A protective system according to claim 2 wherein the inert thickener is selected from silica, titania, fuller's earth, clays, or bentonite.

4. A protective system according to claim 2 wherein the thickener is an inert pyrogenic silica.

5. A protective system according to claim 1 wherein the alkali metal salts are potassium salts.

6. A protective system according to claim 1 containing 4%, or less water.

7. A protective system according to claim 1 containing:
   (i) at least one active ingredient chosen from the potassium salts of phenol, acetophenone oxime, acetone oxime, and 2,3-butanedione monoxime;
   (ii) the macrocycle 4,7,13,16,21,24-hexaoxa-1,10-diazabicyclo[8,8,8] hexacosane; and
   (iii) dioxolane as solvent.

8. A protective system according to claim 1 containing:
   (i) at least one active ingredient chosen from the potassium salts of phenol, acetophenone oxime, acetone oxime, and 2,3-butanedione monoxime;
   (ii) the macrocycle 1,4,7,10,13,16-hexaoxacyclooctadecane; and
   (iii) dioxolane as solvent.

9. A protective system according to claim 1 containing:
   (i) at least one active ingredient chosen from the potassium salts of phenol, acetophenone oxime, acetone oxime and 2,3-butanedione monoxime;

(ii) the macrocycle 4,7,13,16,21,24-hexaoxa-1,10-diazabicyclo[8,8,8] hexacosane; and (iii) tetraglyme containing up to 4% water as solvent.

10. A protective system according to claim 1 containing:
   (i) at least one active ingredient chosen from the potassium salts of phenol, acetophenone oxime, acetone oxime, and 2,3-butanedione monoxime;
   (ii) the macrocycle 4,7,13,16,21,24-hexaoxa-1,10-diazabicyclo[8,8,8] hexacosane; and
   (iii) dimethoxyethane containing up to 1.25% water as solvent.

11. A protective system according to claim 1 containing:
   (i) at least one active ingredient chosen from the potassium salts of acetone oxime and acetophenone oxime;
   (ii) the macrocycle 1,4,7,10,13,16-hexaoxacyclooctadecane; and
   (iii) tetraglyme containing up to 3.0% water as solvent.

12. A protective system according to claim 1 containing:
   (i) at least one active ingredient chosen from the potassium salts of acetone oxime and acetophenone oxime;
   (ii) the macrocycle 1,4,7,10,13,16-hexaoxacyclooctadecane; and
   (iii) dimethoxyethane containing up to 2.5% water as solvent.

13. A protective system according to claim 1 wherein the weight ratio of active ingredient:macrocycle is at most 2:1.

14. A protective system according to claim 1 wherein the weight ratio of active ingredient:macrocycle is substantially 1:1.

* * * * *